(12) United States Patent
Krumm et al.

(10) Patent No.: US 11,821,857 B2
(45) Date of Patent: Nov. 21, 2023

(54) DATA-DRIVEN SOLUTIONS FOR INVERSE ELEMENTAL MODELING

(71) Applicants: Robert Krumm, Oklahoma City, OK (US); Ryan Antle, Oklahoma City, OK (US); Haifeng Jiang, Oklahoma City, OK (US)

(72) Inventors: Robert Krumm, Oklahoma City, OK (US); Ryan Antle, Oklahoma City, OK (US); Haifeng Jiang, Oklahoma City, OK (US)

(73) Assignee: BAKER HUGHES OILFIELD OPERATIONS LLC, Houston, TX (US)

(*) Notice: Subject to any disclaimer, the term of this patent is extended or adjusted under 35 U.S.C. 154(b) by 73 days.

(21) Appl. No.: 17/495,396

(22) Filed: Oct. 6, 2021

(65) Prior Publication Data

US 2022/0107279 A1  Apr. 7, 2022

Related U.S. Application Data

(60) Provisional application No. 63/088,094, filed on Oct. 6, 2020.

(51) Int. Cl.
*G01N 23/20* (2018.01)
*G01N 23/2055* (2018.01)
(Continued)

(52) U.S. Cl.
CPC ......... *G01N 23/223* (2013.01); *E21B 49/005* (2013.01); *E21B 49/06* (2013.01);
(Continued)

(58) Field of Classification Search
CPC ............. G01N 23/20; G01N 23/20008; G01N 23/2005; G01N 23/20091; G01N 23/205;
(Continued)

(56) References Cited

U.S. PATENT DOCUMENTS

| 4,712,424 A | * | 12/1987 | Herron | .................. G01V 11/00 250/269.1 |
| 6,681,187 B2 | * | 1/2004 | Ishii | ...................... G03C 1/005 700/121 |

(Continued)

FOREIGN PATENT DOCUMENTS

WO    2014143166 A1    9/2014

OTHER PUBLICATIONS

Cohen, David and Colin R. Ward. "Sednorm—a program to calculate a normative mineralogy for sedimentary rocks based on chemical analyses." Computers and Geosciences 17.9 (1991): 1235-1253.
(Continued)

*Primary Examiner* — Allen C. Ho
(74) *Attorney, Agent, or Firm* — CANTOR COLBURN LLP

(57) ABSTRACT

Methods for determining mineral compositions of materials are described. The methods include obtaining elemental data associated with a geologic sample, calculating a measurement correlation matrix of the geologic sample from the elemental data, calculating an artificial correlation matrix, comparing the measurement correlation matrix and the artificial correlation matrix to determine an error value, minimizing the error value by updating the artificial correlation matrix and comparing the measurement correlation matrix to the updated artificial correlation matrix, and determining a mineral composition of the geologic sample based on the minimized measurement correlation matrix.

20 Claims, 7 Drawing Sheets

(51) Int. Cl.
  *G01N 23/223* (2006.01)
  *G01N 33/24* (2006.01)
  *G01N 23/207* (2018.01)
  *G01N 23/222* (2006.01)
  *G01N 1/28* (2006.01)
  *G01N 1/34* (2006.01)
  *E21B 49/06* (2006.01)
  *E21B 49/00* (2006.01)
  *G01N 23/2005* (2018.01)
  *G01V 5/04* (2006.01)
  *G01V 5/08* (2006.01)
  *G01V 5/12* (2006.01)

(52) U.S. Cl.
  CPC .............. *G01N 1/286* (2013.01); *G01N 1/34* (2013.01); *G01N 23/20* (2013.01); *G01N 23/2005* (2013.01); *G01N 23/207* (2013.01); *G01N 23/2055* (2013.01); *G01N 23/222* (2013.01); *G01N 33/24* (2013.01); *G01V 5/04* (2013.01); *G01V 5/045* (2013.01); *G01V 5/08* (2013.01); *G01V 5/12* (2013.01); *G01V 5/125* (2013.01); *G01N 2001/2866* (2013.01); *G01N 2223/056* (2013.01); *G01N 2223/076* (2013.01); *G01N 2223/106* (2013.01); *G01N 2223/616* (2013.01)

(58) Field of Classification Search
  CPC .. G01N 23/2055; G01N 23/207; G01N 23/22; G01N 23/223; G01N 2223/076; G01N 2223/1016; G01N 2223/616; G01V 5/04; G01V 5/045; G01V 5/08; G01V 5/12; G01V 5/125
  USPC .......................................... 378/44–50, 70–76
  See application file for complete search history.

(56) References Cited

U.S. PATENT DOCUMENTS

| | | | |
|---|---|---|---|
| 7,495,436 B2* | 2/2009 | Hamdan | G01V 3/32 324/303 |
| 3,101,907 A1 | 1/2012 | Jacobi et al. | |
| 8,093,893 B2* | 1/2012 | Niemeyer | G01R 33/5617 324/303 |
| 8,165,817 B2* | 4/2012 | Betancourt | G01V 11/00 73/152.09 |
| 9,696,453 B2* | 7/2017 | Freedman | G01V 5/12 |
| 10,107,770 B2 | 10/2018 | Weindorf et al. | |
| 10,329,903 B2* | 6/2019 | Ramakrishnan | G01V 3/38 |
| 10,705,246 B2* | 7/2020 | Guo | G01V 5/045 |
| 11,340,207 B2* | 5/2022 | Rocher | G01N 23/2206 |
| 11,579,329 B2* | 2/2023 | Mitchell | G01V 5/12 |
| 2003/0023390 A1 | 1/2003 | Ishii et al. | |
| 2009/0125239 A1 | 5/2009 | Niemeyer et al. | |
| 2013/0297254 A1 | 11/2013 | Vignesh et al. | |

OTHER PUBLICATIONS

Ingram, Wesley. "Multimineral Modeling" Presentation. Weatherford Laboratories. 2015. 33 pages.
International Search Report, International Application No. PCT/US2021/053706, dated Jan. 26, 2022, Korean Intellectual Property Office; International Search Report 3 pages.
International Written Opinion, International Application No. PCT/US2021/053706, dated Jan. 26, 2022, Korean Intellectual Property Office; International Written Opinion 5 pages.
Zhao, Jianpeng, Hui Chen, Lu Yin, and Ning Li. "Mineral inversion for element capture spectroscopy logging based on optimization theory." Journal of Geophysics and Engineering, 14 (2017) 1430-1436.

* cited by examiner

| Depth | LE | Al | Si | Ti | Fe | Mn | Mg | Ca | S |
|---|---|---|---|---|---|---|---|---|---|
| 9404 | 4.579946 | 0.099329 | 0.59814 | 0.006505 | 0.004445 | 0.000141 | 0 | 0.147384 | 0.010931 |
| 9405 | 4.394986 | 0.123941 | 0.662197 | 0.00713 | 0.004633 | 0.000282 | 0.015116 | 0.149522 | 0.011567 |
| 9406 | 4.426939 | 0.113841 | 0.613447 | 0.006505 | 0.004695 | 0.000423 | 0.038657 | 0.163245 | 0.010718 |
| 9407 | 4.40443 | 0.124039 | 0.641233 | 0.006755 | 0.004695 | 0.000423 | 0.023046 | 0.156295 | 0.011249 |
| 9408 | 4.348613 | 0.125706 | 0.636574 | 0.006755 | 0.005259 | 0.000423 | 0.041383 | 0.160037 | 0.011037 |

FIG.2

| Depth | LE | Al | Si | Ti | Fe | Mn | Mg | Ca | S |
|---|---|---|---|---|---|---|---|---|---|
| 9407 | 4.40443 | 0.124039 | 0.641233 | 0.006755 | 0.004695 | 0.000423 | 0.023046 | 0.156295 | 0.011249 |

| Mineral | Formula |
|---|---|
| Quartz | $SiO_2$ |
| Anatase | $TiO_2$ |
| K-spar | $KAlSi_3O_8$ |
| Anorthite | $CaAl_2Si_2O_8$ |
| Albite | $NaAlSi_3O_8$ |

| Depth | Quartz | Anatase | K-spar | Anorthite | Albite |
|---|---|---|---|---|---|
| 9404 | 0.4 | 0.05 | 0.2 | 0.15 | 0.2 |
| 9405 | 0.45 | 0.1 | 0.25 | 0.2 | 0 |
| 9406 | 0.4 | 0.05 | 0.2 | 0.25 | 0.1 |
| 9407 | 0.35 | 0.15 | 0.15 | 0.3 | 0.05 |
| 9408 | 0.4 | 0.1 | 0.2 | 0.25 | 0.05 |

FIG.6

DATA-DRIVEN SOLUTIONS FOR INVERSE ELEMENTAL MODELING

CROSS REFERENCE TO RELATED APPLICATIONS

This application claims the benefit of an earlier filing date from U.S. Provisional Application Ser. No. 63/088,094, filed Oct. 6, 2020, the entire disclosure of which is incorporated herein by reference.

BACKGROUND

1. Field of the Invention

The present invention generally relates to downhole operations and systems, and particularly to data-driven solution for inverse elemental modeling.

2. Description of the Related Art

Boreholes are drilled deep into the earth for many applications such as carbon dioxide sequestration, hydrogen storage, helium production, geothermal production, mineral exploration and production, and hydrocarbon exploration and production. In all applications, boreholes are drilled such that they pass through or allow access to a material (e.g., a gas or fluid) contained in a formation (e.g., a compartment) located below the earth's surface. Different types of tools and instruments may be deployed in boreholes to perform various tasks and measurements.

Various sensors may be used for logging and measurements during drilling operation (e.g., measurement-while-drilling and logging-while-drilling). Typically, such measurements are conducted downhole using wireline or while-drilling systems. Surface-based data typically is limited and may include surface-based x-ray diffraction (XRD) and x-ray fluorescence (XRF) analysis performed on cores or samples to determine element and/or mineral data. Improved data collection and while-drilling analysis may be beneficial to the industry.

There has long been a need for open-hole logging tools and methods that are capable of providing measurements of the lithology and mineralogy of a geologic formation in selected directions, providing measurements of the mineralogy and lithology both close to the bore hole and deep into the subterranean formation, and providing all such measurements with high vertical and lateral resolution. Quantitative information about the reservoir rock lithology and associated minerals is important not only for determining the producing potential for a specific formation, but for making technical and business decisions in hydrocarbon exploration and exploitation as well. For example, exploration geologists can use rock mineralogy information associated with subterranean formations to reduce the risk in discovering hydrocarbons by determining the thermal and diagenetic history of the specific formation, defining the provenance (source area) and the depositional environments of the sediments in the formation, and correlating certain minerals with well logs. Formation mineralogy information can also be used during the exploration process to assess reservoir quality, develop effective depletion strategies, and predict the effect of rock-fluid interactions. During production processes, formation mineralogy can be used to design workover and completion strategies, such as selection of drilling fluids and proper stimulation methods (e.g., effective acidizing or fracturing applications).

The interpretation of formation lithology, both general and specific, is also important. For example, quantitative knowledge of the lithological constituents in a subterranean formation surrounding a well, as a function of depth, could be valuable in assessing all aspects of exploration, evaluation, production and completion. For example, suitable applications could include regional studies of facies architectures, estimating distributions of reservoir facies, quantifying amounts of clay materials in all layers, identifying subtle and pronounced changes in depositional or diagenetic facies by characterizing the formation minerals, and planning enhanced recovery strategies.

Traditional methods of determining subterranean formation lithology and mineralogy have used cores from wellbores, which are often analyzed using X-ray diffraction techniques and the like. However, such traditional methods are very time-consuming, and are not efficient for use in exploration applications.

SUMMARY

Disclosed herein are methods for determining mineral compositions of materials are described. The methods include obtaining elemental data associated with a geologic sample, calculating a measurement correlation matrix of the geologic sample from the elemental data, calculating an artificial correlation matrix, comparing the measurement correlation matrix and the artificial correlation matrix to determine an error value, minimizing the error value by updating the artificial correlation matrix and comparing the measurement correlation matrix to the updated artificial correlation matrix, and determining a mineral composition of the geologic sample based on the minimized measurement correlation matrix.

BRIEF DESCRIPTION OF THE DRAWINGS

The subject matter, which is regarded as the invention, is particularly pointed out and distinctly claimed in the claims at the conclusion of the specification. The foregoing and other features and advantages of the invention are apparent from the following detailed description taken in conjunction with the accompanying drawings, wherein like elements are numbered alike, in which:

FIG. 2 is an example of elemental data table from a geologic sample that may be investigated in accordance with embodiments of the present disclosure;

FIG. 3 is representative of a vector of elemental abundances within the geologic sample from the table of FIG. 2;

FIG. 5 is an example of a portion of a mineral dictionary illustrating mineral names and associated chemical formulas that is employed with embodiments of the present disclosure;

FIG. 6 is an example of a mineralogy output spreadsheet from a data-driven element-to-mineral model in accordance with an embodiment of the present disclosure;

DETAILED DESCRIPTION

Figure 1:
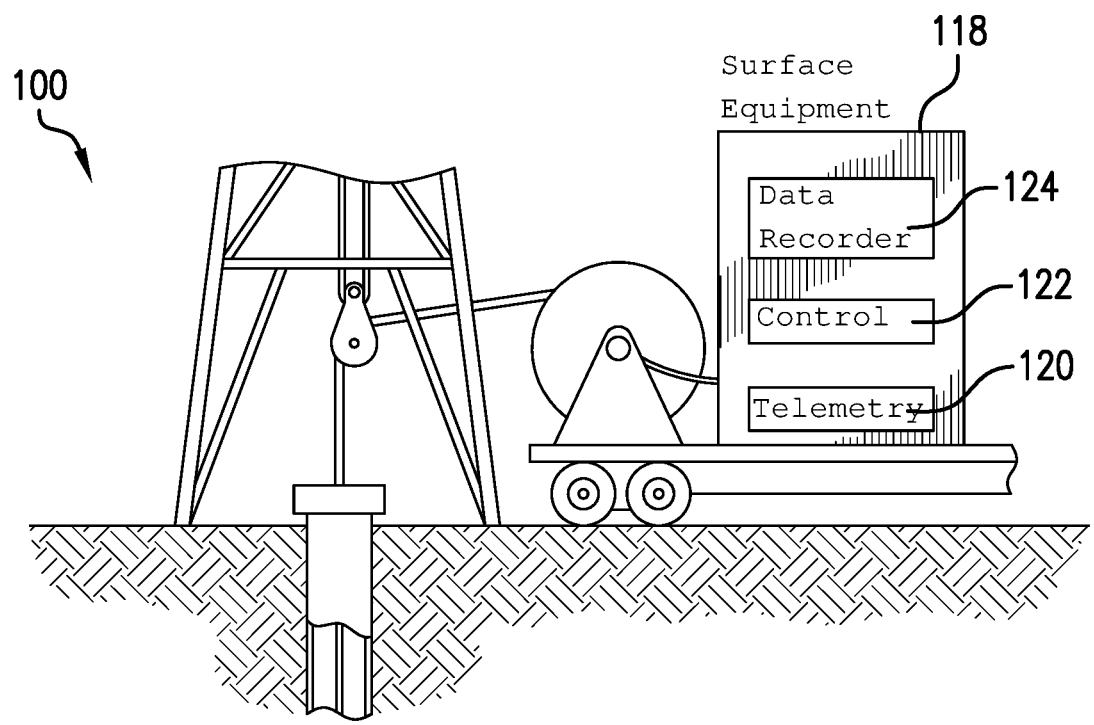
FIG. 1 is an example of a system for performing downhole operations that can employ embodiments of the present disclosure.
Figure 1:
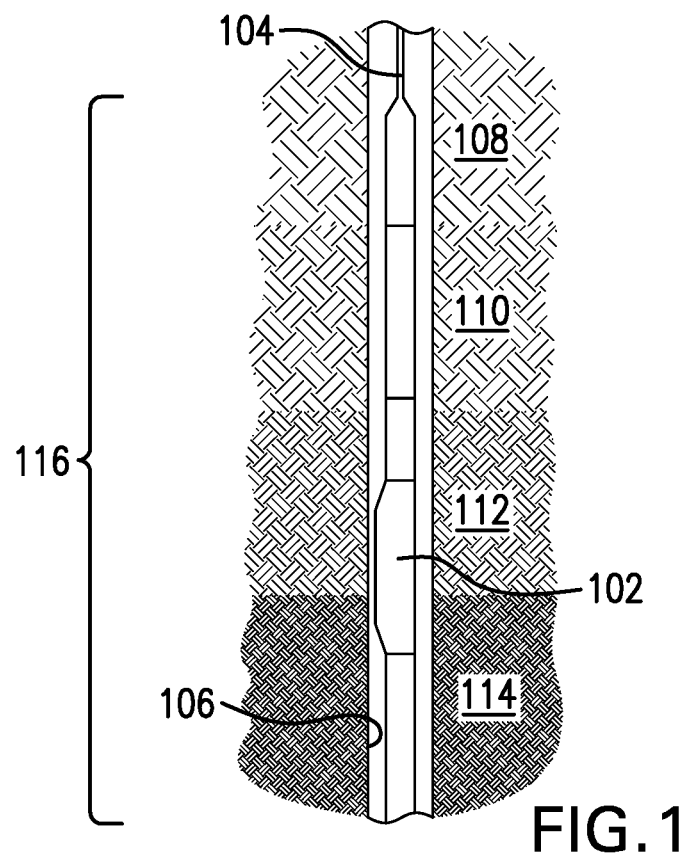

FIG. 1 is illustrative of a system 100 for downhole or subsurface investigations and operations. The system 100 may be configured as a drilling system that is capable of drilling or forming a borehole within the Earth. In other configurations, the system 100 may be a post-drilling system, such as a production system. In either case, equipment and/or tools may be deployed downhole from the surface system and into the borehole.

FIG. 1 illustrates a logging tool 102 for use with the methods and processes described in the present disclosure. The logging tool 102 is illustrated as a wireline tool that is suspended from a cable 104. In other configurations, the logging tool 102 may be configured as a module or sub that is installed along a drill string or as part of a bottomhole assembly, as will be appreciated by those of skill in the art.

The logging tool 102 is deployed in a wellbore 106 drilled through earth formations 108, 110, 112, and 114 in order to make measurements of properties of one or more of the formations 108, 110, 112, and 114. The wellbore 106 in FIG. 1 can be filled with a liquid suspension, known in the art as "drilling mud." In accordance with aspects of the present disclosure, the terms "wellbore" or "borehole," as used herein, include, but are not limited to, cased wellbores, partially-cased wellbores, and non-cased wellbores. A tool string 116 of one or more logging tools (including logging tool 102) can include a neutron apparatus as well as a plurality of additional logging tools, sampling tools, investigation and/or sensing tools, sondes, etc., as will be appreciated by those of skill in the art.

As noted, the logging tool 102 (and the tool string 116) is lowered into the wellbore 106 by a means of a cable 104. The cable 104 may be an armored electrical cable or similar structure. The cable 104 can be spooled and unspooled from a winch or drum, as will be appreciated by those of skill in the art. The tool string 116 may be electrically connected to surface equipment 118 by an insulated electrical conductor (not shown in FIG. 1) forming part of the cable 104.

The surface equipment 118 can include one part of a telemetry system 120 for communicating control signals and data between the tool string 116 and a surface control unit 122 (e.g., computer or other processing systems or structure). The surface control unit 122 may be connected to a data recorder 124 for recording measurements made by logging tool 102 and/or other components of the tool string 116 and transmitted to the surface equipment 118.

In some configurations in accordance with the present disclosure, the logging tool 102 can include a downhole processor coupled to one or more electromagnetic radiation systems or sources, as appreciated by those of skill in the art. The downhole processor can be contained within, or is directly associated with, the logging tool 102. In accordance with aspects of the present disclosure, the logging tool 102 may be a sampling tool that is configured to extract a core, a sidewall core, or a cutting (depending on when and where the logging tool 102 is deployed). In this configuration, the logging tool 102 is configured to extract and obtain a geologic sample (e.g., core, core sample, cutting, cutting sample, etc.). The geologic sample may then be analyzed downhole in the logging tool 102 or may be retrieved back to the surface, for surface-based analysis.

Once obtained, a geologic sample (core, sidewall core, or cutting) is prepared for measurement. For example, samples may be slabbed with a slabbing saw and the freshly slabbed surface is cleaned, surface salts are removed, and measurements are done on the freshly exposed surface. In another embodiment, the geologic sample is trimmed and a freshly exposed surface is cleaned, surface salts are removed, and measurements are done on the freshly exposed and cleaned surface. In yet another embodiment the geological samples (which may be obtained during a drilling operation) may be washed, dried, and ground into powder which is pressed into pellets and measurements are done on the pellet surface.

In accordance with embodiments of the present disclosure, the measurements are acquired on prepared geologic samples using an x-ray fluorescence instrument. X-ray fluoroscopy works as follows. X-rays of a certain, specific, or predetermined energy (e.g., 10-40 keV) are directed at or bombarded upon atoms of the geologic sample to excite inner shell electrons causing the inner shell electrons to leave the atoms. As a result of the lost electron, a higher shell electron will move into the inner shell to fill the vacancy. When the higher shell electron drops to the lower shell, a characteristic x-ray is emitted from the atom and the emitted x-ray is measured by an instrument or detection device.

The detection device is configured to measure the energy of the emitted x-ray to determine an elemental signature. For example, an instrument may be calibrated based on a manufacturer's specification to convert a received or detected x-ray spectrum into elemental abundances of the geologic sample. This elemental data may be stored in electronic or digital memory and in some configurations may be presented in spreadsheet form.

Determining mineralogical makeup of rock (or other compounds made up of components with similar proportions of various elements) from elemental information is common practice for fields like geoscience, petrophysics, metallurgy, forensics, quality control, etc. Inverse modeling is the process of taking measured data and postulating a set of conditions that would recreate those measurements. As noted above, the measured data are proportions of elements or elemental data associated with a geologic sample. A sample set may be defined as a group of element data or element proportions of a geologic sample. The conditions that satisfy the quantities of elements in the sample set are assemblages of constituents made up of said elements. Depending on the application, the constituents could be minerals, alloys, chemical products, etc.

Elemental inversion models reconstruct the constituents of materials from elemental data (e.g., minerals). Elemental data can come from X-ray Fluorescence, Mass Spectrometry, Emission Spectrometry, Wet Chemistry, and Chromatography, among other measurements. A classic example of inverting elemental data into proportions of constituents comes from oilfield industry where elemental data is collected with elemental capture spectroscopy logging tools, this elemental data is inverted into its constituents, i.e., minerals. The challenge facing element inversion models is knowing what constituents should be included in the inversion. The current state of the art is model-constituents being selectively guided by a priori knowledge or a learned experience of the system. While this current method produces inversion models that deliver reliable results, it precludes the possibility of robust models with a library of constituents.

Further, in many applications, the constituents making up the subject of investigation have similar elemental compositions. For example, the mineral Muscovite has the molecular formula $KAl_2(Si_2Al)O_{10}(OH)_2$ while its derivative, Illite, has a similar molecular formula, $K_{1.5}Al_4(Si_{6.5}Al_{1.5})O_{20}(OH)_4$. While these two minerals have similar elemental compositions, other properties (e.g., petrophysical properties including, for example, mechanical strength) differ greatly. Accordingly, ensuring accurate and correct identification of a mineral based on an elemental composition is important and can significantly impact downstream decision-making. However, keeping both minerals in an element-to-mineral (ETM) inversion model results in the model being over-defined. Such over-defined ETM can yield unrealistic mineral assemblages.

Inversion models often rely on knowledged-inputs that limit the number of constituents. Knowledged-inputs are inputs or bounds related to potential mineral outputs associated with a specific location, field, formation, etc. For example, knowledged-input can include bounds imposed by a human operator that is knowledgeable regarding a given location or formation. Other types of knowledged-inputs can include large datasets or databases related to known information associated with a geological location and/or geological formation. Such constraints are regional or field or even formation specific, and thus each time analysis is done, different knowledged-inputs will be required.

An alternative process may rely upon data-driven techniques. Such data-driven techniques, such as Artificial Neural Networks (ANNs) or Random Forest Networks (RFNs), for example, require large datasets for the machine learning to be able to process many different combinations and extract out bounds or limits for reducing the number of constituents for an inversion model. The large datasets may require many different cores or samples to be processed and prepared, and then analyzed, as described above. Such processes may require thousands of data points and reference sets to enable the machine learning associated therewith. That is, although such processes can eliminate human input, such data sets are hard to compile and further are not as adaptable to a given region—i.e., preliminary data is still required as a benchmark.

Embodiments of the present disclosure are not so limited and do not require any knowledged-data for operation. In contrast, a different method for restricting the number of inputs into an element inversion model that uses a library of potential constituents and statistical properties of the elemental input is provided herein. Advantageously, embodiments of the present disclosure can reduce the dimensionality of the elemental inversion without removing inputs. In contrast, a correlation method and process is employed to reduce the number of mineral possibilities without the need for knowledged-data (or location specific) data/inputs.

In accordance with embodiments of the present disclosure, in operation, a correlation matrix of measured elemental data is compared with a correlation matrix of statistically generated populations of constituents. A solver minimizes the difference in error between the correlation matrices by adjusting the means of the statistically generated components. Components are determined to be "included" or "not included" in the inversion model based on the absolute value of their respective mean from the converged solution. As such, large datasets and/or large numbers of geologic samples are not required to determine an elemental and mineralogical composition of a formation from which the geologic samples are obtained.

Advantageously, embodiments of the present disclosure provide for significantly improved processes for determining mineralogy regarding a formation. Specifically, the amount of time and the number of data points may be significantly reduced as compared to knowledged-data systems or machine-learning systems. Embodiments of the present disclosure do not require large datasets, only enough samples to develop statistical relations. For example, as compared to prior machine-based systems, embodiments of the present disclosure may require 10% or fewer data points than that required for alternative machine-learning systems and methods.

Advantageously, the methods of the present disclosure can be run without any a priori knowledge about the subject, expertise in the field, or even knowledge regarding a given formation. Using statistically generated mixtures of the subject's components imitates natural processes, and thus an efficient process is achieved.

As noted above, embodiments of the present disclosure are directed to efficiently extract and determine a formation composition (e.g., minerals) using a method involving correlation processes based on a known set of elemental data. Correlation is the joint variability of two variables in a dataset and may include, in some respects, a linear regression. Two variables can trend positively together, trend in opposite directions, or have no relationship. A correlation matrix represents these tendencies for all variables in a dataset.

In the context of elemental to constituent inversions, the dataset is almost always elemental abundances expressed in terms of weight or moles. Population samples contain variability. In this context, it is the variability of elemental compositions. There can also be variability in measurements done on the exact same sample. It is from these measurement distributions that a correlation matrix may be calculated. It is important when calculating the correlation matrix that the measurements are restricted to a specific type or class of sample. As such, a measurement correlation matrix may be established. With the correlation of the geologic sample set calculated (measurement correlation matrix), another correlation matrix is generated from an artificial data set (artificial correlation matrix). The artificial dataset is calculated using statistically defined (e.g. Gaussian) and random proportions of constituents from an input library. These proportions are converted into elemental abundances using the constituent's molecular formula and the artificial correlation matrix is calculated. An optimization function can be used to minimize the differences between the measured dataset and the artificial dataset by changing the means of the distributions of constituents. That is the measurement correlation matrix is compared to the artificial correlation matrix. The constituents are included in a resulting inversion model if an optimized mean exceeds a certain or predetermined threshold value.

With references to FIGS. 2-7, an example process in accordance with an embodiment of the present disclosure will be described. The description that follows is merely an example process in accordance with the present disclosure.

Turning to FIG. 2, an example of elemental data from a geologic sample can be seen in Table 200. The data illustrated in Table 200 is x-ray fluorescence data reflective of elemental composition of the geologic sample. The geologic sample may be a core sample, a sidewall core sample, a cuttings sample, etc., as will be appreciated by those of skill in the art. The geologic sample is a physical sample of material from a downhole or subsurface formation. The geologic sample may be prepared for investigation and testing, as described above.

As shown, the first column of Table 200 represents depth measurements. That is, each row of Table 200 represents data collected from different depths from a subsurface formation, such as along a borehole or wellbore. The geologic samples may be obtained downhole using a logging tool, a sampling tool, a coring tool, or at the surface by obtaining the geologic sample from drilling mud and cuttings therein. In Table 200, in order, the columns represent: Light Elements (LE) (e.g., elements having atomic numbers below 12); aluminum (Al) abundance of the geologic sample; silicon (Si) abundance of the geologic sample; titanium (Ti) abundance of the geologic sample; iron (Fe) abundance of the geologic sample; manganese (Mn) abundance of the geologic sample; magnesium (Mg) abundance of the geologic sample; calcium (Ca) abundance of the geologic sample; and potassium (K) abundance of the geologic sample. The XRF elements measured in a real-world geologic sample are not limited to those represented in Table 200, and the illustrated elements are merely provided for illustrative and explanatory purposes.

Data in the form of a table like that in Table 200 is an input for the Data Driven Mineral Model in accordance with embodiments of the present disclosure. Each depth (row of Table 200) represents a vector (i.e., a 1×N matrix) of elemental abundances, where N is the number of elements detected within a given geologic sample. This is represented in FIG. 3, and Table 300, which is representative of a vector 302 of elemental abundances within the geologic sample (e.g. a vector obtained from Table 200 at depth 9407). The vector 302 shown in Table 300 includes the same elemental abundances as that shown in Table 200, given that vector 302 of Table 300 is merely one row of data from the Table 200.

A correlation matrix is calculated for the XRF input data. That is, a measurement correlation matrix is calculated based on the experimental data in Table 200 shown in FIG. 2. A correlation matrix is an N×N matrix where N is the number of experimental variables, in this case elemental abundances. The correlation matrix is defined as:

$$R = \begin{pmatrix} 1 & \cdots & r_{1m} \\ \vdots & \ddots & \vdots \\ r_{n1} & \cdots & 1 \end{pmatrix} \quad (1)$$

$$r_{jk} = \frac{S_{jk}}{S_j S_k} = \frac{\sum_{i=1}^{n}(X_{ij} - \overline{X_j})(X_{ik} - \overline{X_k})}{\sqrt{\sum_{i=1}^{n}(X_{ij} - \overline{X_j})^2} \sqrt{\sum_{i=1}^{n}(X_{ik} - \overline{X_k})^2}}$$

In equation (1), R is the correlation matrix, $r_{jk}$ is the correlation between the j-th and k-th column of the data matrix X (e.g., Table 200), $S_{jk}$ is the covariance between j-th and k-th column of the data matrix X, $X_{ij}$ is an element from the data matrix X (e.g., Table 200), the subscripts i and j refer to the rows and columns of data matrix X, respectively, n, m refer to the respective number of rows and columns in the data matrix X (e.g., Table 200) and $\overline{X_k}$ denotes an average of the elements in the k-th column from the data matrix X.

Figure 4:
FIG. 4 is an example correlation matrix for measured elemental abundances in accordance with an embodiment of the present disclosure.

An example correlation matrix for measured elemental abundances can be found in Table 400 of FIG. 4. Correlation values range between −1 to +1, with positive values being positively correlated and negative values being negatively correlated. The magnitude of the correlation is the strength of the correlation; values of +1 or −1 are more strongly correlated than values of −0.5 or +0.5. In the example of pyrite, which has a chemical formula of $FeS_2$, we would expect iron (Fe) and sulfur (S) to be strongly correlated if present in the geologic sample.

It is known that certain minerals naturally trend with positive or negative correlation. That is, certain minerals may have a positive correlation where two or more minerals are typically present together or at least are highly likely to appear together. In other cases, certain minerals may never or almost never appear together, or at least have a highly unlikely chance of appearing together in a given geologic sample. Example minerals are represented with chemical formulas (Table 500 shown in FIG. 5). The example mineral list in Table 500 is not to be exhaustive, but merely is an example list of minerals that may be found in geologic samples obtained from downhole or subsurface formations. The list provided in Table 500, and similar lists, establishes a mineral dictionary of mineral names and chemical formulas, which may be a user-defined input to the inversion model. Like the elements listed in Table 200, the mineral inputs of Table 500 are not limited to those represented in Table 500, and such list of minerals is merely for illustrative and explanatory purposes.

In accordance with an example embodiment of the present disclosure, a correlation matrix of artificial data is generated using the mineral dictionary having mineral names and chemical formulas of the listed minerals. That is, an artificial correlation matrix is generated. The artificial correlation matrix is generated through the following process. A proposed initial mineral abundance table or list is set as an initialization point. At all times throughout the process, mineral abundances sum to one—i.e., the mineral abundances sum to one because they represent the composition of a geologic sample. The artificial correlation matrix represents the correlations between different elements and minerals within an artificial geologic sample. That is, given an arbitrary or best guess set of minerals within a geologic sample, an artificial correlation matrix is generated.

Mineral abundances are converted into molar abundances using the molecular weight of each given mineral. Molar abundances are used with the chemical formulas to calculate individual elemental abundances. As such, each mineral and associated mineral abundance is converted into an elemental abundance. From this, a single point of artificial data is generated by summing the contribution of each element for all minerals. This is the "artificial XRF" or artificial correlation matrix. Equation (2), below, is a method of converting a proposed mineral composition to a theoretical response.

$$(\text{Mineral}_1 \ \cdots \ \text{Mineral}_M) \times \begin{pmatrix} \text{Element}_{11} & \cdots & \text{Element}_{1N} \\ \vdots & \ddots & \vdots \\ \text{Element}_{M1} & \cdots & \text{Element}_{MN} \end{pmatrix} = \begin{pmatrix} E_1 \\ \vdots \\ E_N \end{pmatrix} \quad (2)$$

In equation (2), a proposed composition (e.g., $\text{Mineral}_1$, $\text{Mineral}_2$, up to $\text{Mineral}_M$) is combined with stoichiometry elemental data (e.g., $\text{Element}_{11}$, $\text{Element}_{1N}$, $\text{Element}_{M1}$, up to $\text{Element}_{NM}$) to obtain a theoretical response (e.g., $E_1$, $E_2$, up to $E_N$). An example of such theoretical response is illustrated below in equation (3):

$$(0.0083 \text{ mol} \quad 0.0042 \text{ mol}) \times \begin{pmatrix} 1 & 2 & 0 & 0 \\ 0 & 0 & 1 & 2 \end{pmatrix} = \begin{pmatrix} 0.0083 \text{ mol Si} \\ 0.0166 \text{ mol O} \\ 0.0042 \text{ mol Fe} \\ 0.0084 \text{ mol S} \end{pmatrix} \quad (3)$$

In equation (3), in the first vector (also referred to as "the proposed composition"), the first and second element stands for the amount of $SiO_2$ and $FeS_2$, respectively, within the composition. The matrix in equation (3) (also referred to as "the stoichiometry matrix" or simply "the stoichiometry" contains the values that are to be multiplied with the proposed composition to yield the last vector (also referred to as "the theoretical response"). As one example, for an artificial data point consisting of a 50/50 weight ratio of quartz ($SiO_2$) and pyrite ($FeS_2$), the following may be found:

$$\frac{0.5 \text{ wt \% } SiO_2}{60.08 \text{ g/mole}} = 0.0083 \frac{\text{mol}}{\text{g}} SiO_2 \quad (4)$$

$$0.008322 \frac{\text{mol}}{\text{g}} SiO_2 * 1Si = 0.0083 \frac{\text{mol}}{\text{g}} Si$$

$$0.008322 \frac{\text{mol}}{\text{g}} SiO_2 * 2O = 0.0166 \frac{\text{mol}}{\text{g}} O$$

$$\frac{0.5 \text{ wt \% } FeS_2}{119.98 \text{ g/mol}} = 0.0042 \frac{\text{mol}}{\text{g}} FeS_2$$

$$0.0042 \frac{\text{mol}}{\text{g}} FeS_2 * 1Fe = 0.0042 \frac{\text{mol}}{\text{g}} Fe \quad (5)$$

$$0.0042 \frac{\text{mol}}{\text{g}} FeS_2 * 2S = 0.0084 \frac{\text{mol}}{\text{g}} S$$

The molecular weights of quartz and pyrite are 60.08 g/mol and 119.98 g/mol, respectively. Accordingly, in this example and as shown in equations (4) and (5), the geologic sample has 0.00832 mol/g of silicon (Si), 0.0166 mol/g of oxygen (O), 0.0042 mol/g of iron (Fe), and 0.0084 mol/g of sulfur (S). These calculations are summarized in matrix form in example equation (3) above.

The above described process for converting into molar abundance and then calculating individual element abundances (e.g., equation (2)) may be repeated hundreds to thousands of times with added noise to give the artificial correlation matrix statistical representativeness. The repeated process may be employed to give the artificial data some statistical significance. Noise is added to the artificially generated XRF dataset to simulate noise inherent in laboratory measurement and to simulate variability in geologic samples. The noise, as used herein, is a random sampling of a statistical distribution, e.g., a Gaussian distribution. A correlation matrix (artificial correlation matrix) is calculated in the same manner as described above with respect to Table 400 of FIG. 4.

Individual elements from the measurement correlation matrix may then be subtracted from corresponding elements (e.g., same row/column) in the artificial correlation matrix. The sum of the squared difference of the elements in the two matrices is the objective function for an optimization solver. The result is an error value.

In one non-limiting example embodiment, correlation data for a measured geologic sample (e.g., a measurement correlation matrix or "actual XRF") and correlation data for an artificial sample (e.g., artificial correlation matrix or "artificial XRF") may be used for an optimization solver. When subtracting the elements of the measurement correlation matrix from the elements of the artificial correlation matrix the error value is obtained. The error value, which may range between 0 and 1 (for example), represents how close the actual or measured sample is to the artificial mineral set. An element-by-element analysis may be performed in accordance with embodiments of the present disclosure. For example, each element (output) of the resulting optimization solver is a correlation (or error value) of an atomic element j with an atomic element k. In one non-limiting example, if element j is iron and element k is sulfur, and iron has a positive correlation with sulfur, the output of the optimization solver will indicate such correlation as an error value. The differences between the elements of the "Artificial XRF" and the "Actual XRF" are squared (ensuring a positive number) and summed.

An optimization process may iterate over the proposed mineral composition, changing mineral abundances until the differences between the two correlation matrices (e.g., error values) is minimized (i.e., as close to zero as possible). For example, the error value may be a number between 0 and 1 and a predetermined minimum may be established (e.g., 0.1) to set when the process has been sufficiently minimized to provide a relatively high confidence level of the mineralogy output (i.e., reduced error between modeled and natural tendencies).

In some configurations, minerals with abundances higher than a threshold amount, for example a predefined fixed weight-percentage (e.g., 5 wt %), may be used in another (additional or subsequent) iterative solver. Thresholding minerals by a fixed abundance reduces the probability of unlikely mineral candidates being included in the calculated result; the library of minerals is reduced. A second iterative solver may be employed to calculate element amounts for each measurement point with the reduced mineral library and solves mineral abundances by iteratively guessing and checking mineral abundances. The best solution of the iterative solver is where the differences between the calculated elemental abundances and measured elemental abundances are minimized, the proposed mineral composition where this is calculated is recorded. Reducing the number of minerals in the second solver increases the probability of a unique solution.

FIG. 6 illustrates a Table 600 that is an example of a mineralogy output spreadsheet from a data-driven element-to-mineral model in accordance with an embodiment of the present disclosure. This may also be represented as a mineralogy log generated from XRF measurements and the data-driven element-to-mineral model, shown as Plot 700 in FIG. 7. In Plot 700, the x-axis is depth (in feet) and the y-axis is mineral abundance (in weight-percent).

Figure 8:
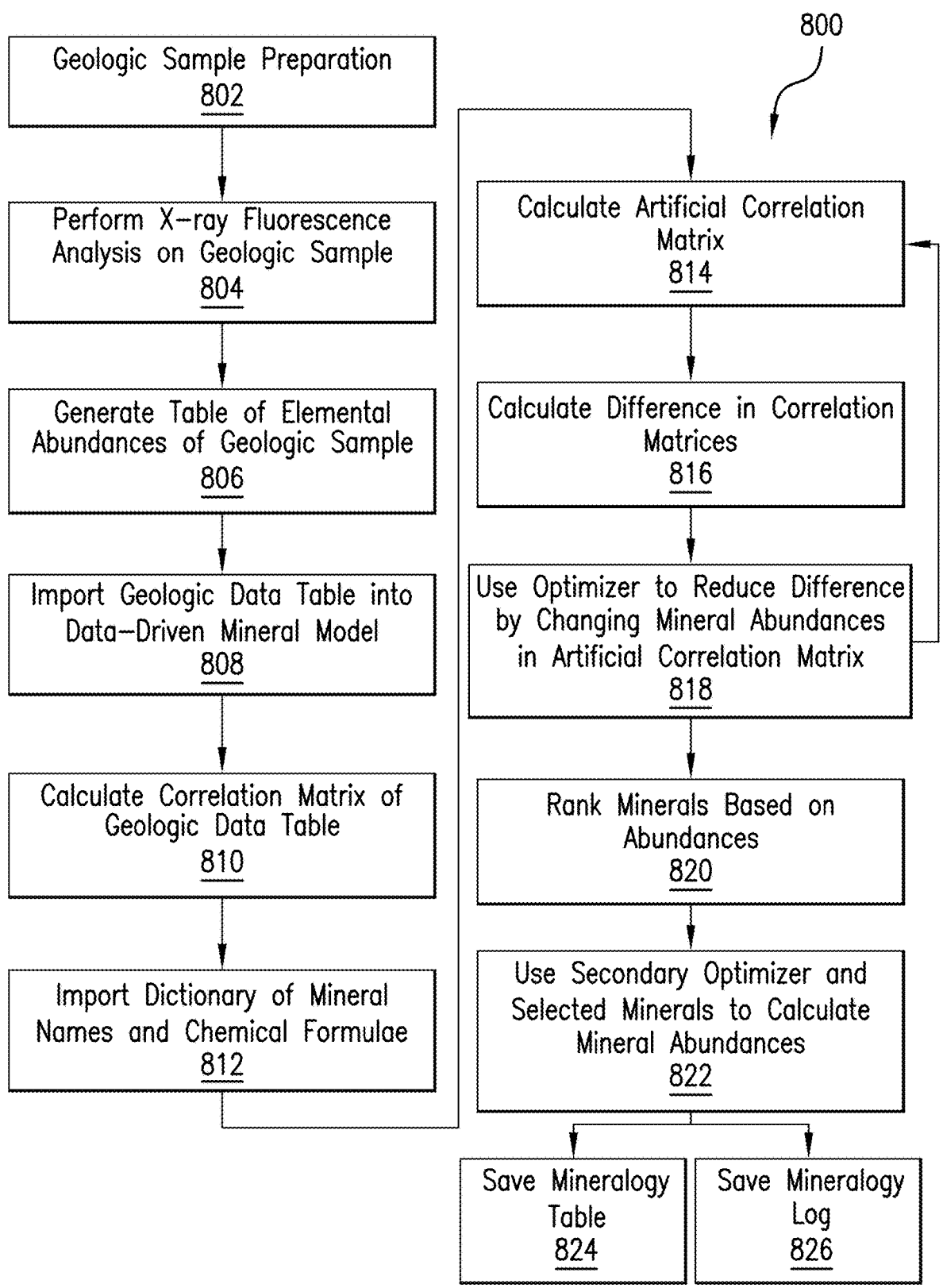
FIG. 8 is a flow process for determining a mineral composition of a geologic sample in accordance with an embodiment of the present disclosure.

Turning now to FIG. 8, a flow process 800 in accordance with an embodiment of the present disclosure is shown. The flow process 800 represents a data-driven correlation process for determining mineral composition of a geologic sample based on X-ray Fluorescence measurements of the geologic sample. The geologic sample may be obtained through any known means, such as core sampling, sidewall core sampling, cuttings extraction, etc., as will be appreciated by those of skill in the art.

At block 802, the geologic sample is prepared for analysis. For example, core samples are slabbed with a slabbing saw and the freshly slabbed surface cleaned, surface salts are removed, and measurements are done on the freshly exposed surface. In the case of sidewall core samples, the geologic sample is trimmed and a freshly exposed surface is cleaned, surface salts are removed, and measurements are done on the freshly exposed and cleaned surface. In the case of cuttings samples (which may be obtained during a drilling operation), the geologic sample is washed, dried, and ground into powder which is pressed into pellets and measurements are done on the pellet surface.

At block 804, X-ray Fluorescence analysis is performed on the prepared geologic sample. During this process, X-rays of a certain, specific, or predetermined energy (e.g., 10-40 keV) are directed at or bombarded upon atoms of the geologic sample to excite inner shell electrons causing the inner shell electrons to leave the atoms. As a result of the lost electron, a higher shell electron will move into the inner shell to fill the vacancy. When the higher shell electron drops to the lower shell, a characteristic x-ray is emitted from the atom and the emitted x-ray is measured by an instrument or detection device. The detection device is configured to measure the energy of the emitted x-ray to determine an elemental signature. For example, an instrument may be calibrated based on a manufacturer's specification to convert a received or detected x-ray spectrum into elemental abundances of the geologic sample. This elemental data may be stored in electronic or digital memory and in some configurations may be presented in spreadsheet form.

At block 806, a table of elemental abundances of the geologic sample is generated. The table of elemental abundances represents the makeup or composition of the geologic sample in terms of elements, but not minerals. The relative amounts of each element present within the geologic sample is entered into the formed table of elemental abundances.

At block 808, the table of elemental abundances of the geologic sample is imported into a data-driven mineral model. The data-driven mineral model employs a correlation technique, as described above.

At block 810, the data-driven mineral model is employed to convert and calculate a measurement correlation matrix, as described above. A measurement correlation matrix may be obtained for each vector of the table of elemental abundances.

At block 812, a mineral dictionary of mineral names and chemical formulae are imported into the data-driven mineral model. The selection of the mineral names and associated chemical formulae may be selected by a user. Further, in some embodiments, the selection of minerals may be based on known properties or characteristics. For example, certain minerals may be known to be within a given formation, but the specific makeup and composition (e.g., mineral quantities) is not known. The flow process 800 is configured to determine the specific makeup and composition of the formation, based in part, upon the mineral dictionary. It will be noted that a mineral dictionary may be pre-stored within a system, and thus the specific temporal relationship between block 812 and the other blocks of flow process 800 is not to be limiting by this example. In some configurations, the mineral dictionary may be downloaded from a remote location (e.g., web-based location).

At block 814, an artificial correlation matrix is calculated. A proposed initial mineral abundance table or list is set as an initialization point. At all times throughout the process, mineral abundances sum to one—i.e., the mineral abundances sum to one because they represent the composition of an artificial geologic sample. The initial table of minerals can be used to generate a correlation matrix associated with the various relative abundance of minerals/elements.

At block 816, the measurement correlation matrix and the artificial correlation matrix are compared. Specifically, the difference between the two matrices is obtained. The output from this comparison is an error value, which represents the disparity between the proposed artificial mineral makeup (as represented by the artificial correlation matrix) and actual mineral makeup of the measured geologic sample (as represented by the measurement correlation matrix).

At block 818, an optimizer is used to reduce the difference (i.e., the error value) by changing the mineral abundances in the artificial correlation matrix. Accordingly, at block 818, blocks 814, 816 are repeated with a new artificial correlation matrix in an effort to reduce the error value to or below a threshold error value. For example, the process of blocks 814-818 may be repeated until the error value drops below a certain (e.g., predetermined) amount (e.g., below 1%). As such, the process, at block 818, performs an updating process such that the selected mineral composition of the artificial correlation matrix is updated each time in an iterative process. By changing the mineral composition at this stage, the error value may be reduced. For example, one mineral is changed at a time and the result on the calculated error is recorded. In this process, if an increase in a certain mineral causes the error to increase, the abundance of said mineral may be decreased in the next iteration. After the error can no longer be reduced for a mineral, the solver moves on to the next mineral. After the solver iterates through all the minerals, the solver will return to the first mineral and determine if any further adjustments reduce the error. It will be noted that this is merely one example of an iterative process for error minimization in accordance with embodiments of the present disclosure. It will be appreciated that other types of minimization, solvers, steps, and processes may be employed without departing from the scope of the present disclosure. At each iteration, the model includes an updated artificial correlation matrix, which is updated in order to more closely match the measurement correlation matrix (e.g., minimizing the error value).

At block 820, after the optimizer of block 818 is complete, the minerals of the resulting error-reduced correlation matrices will be ranked. That is, based on the best fit process of block 818, a specific table of minerals is determined that is a best match for the measured geologic sample composition. With this best fit, the process determines and outputs the mineral makeup or composition of the geologic sample. With the determination of the minerals that comprise the geologic sample, the various minerals may be ranked based on abundance.

At block 822, an optional secondary optimizer may be employed with selected minerals to calculate mineral abundances. This secondary optimization entails inputting a reduced list of minerals (ranked at block 820) and the experimental XRF data. An optimization solver tries to match the elemental abundances for each measurement by iteratively proposing and checking mineral proportions. The mineral composition is considered solved when the difference between the XRF elemental composition and the element composition calculated from the proposed mineral abundances can no longer be reduced.

Figure 7:
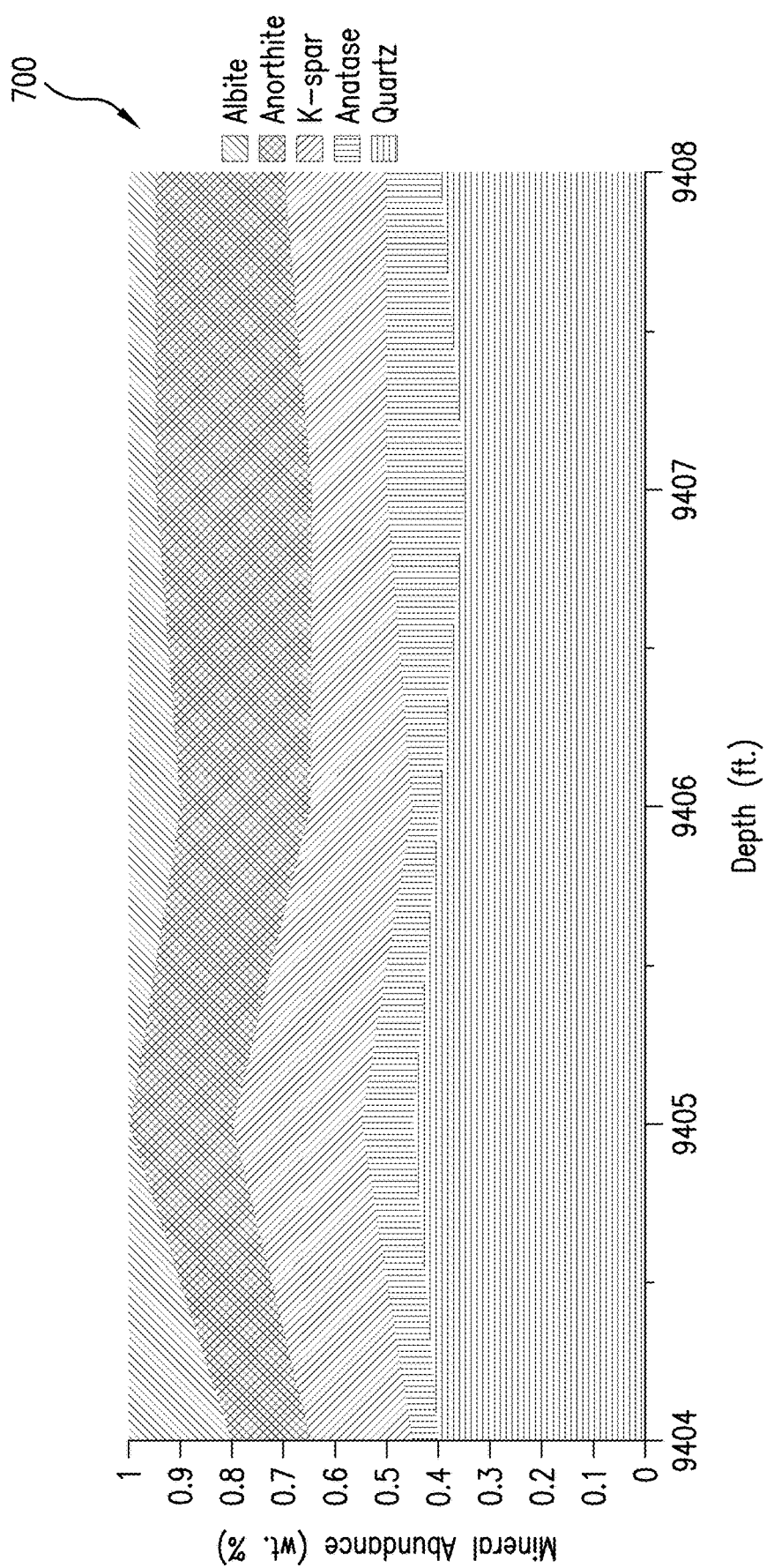
FIG. 7 is an example of a mineralogy output log from a data-driven element-to-mineral model in accordance with an embodiment of the present disclosure.

At blocks 824, 826, different formats of the output may be saved into storage media—such as digital or computer memory. At block 824, a mineralogy table of the geologic sample is saved (e.g., as shown in FIG. 6). At block 826, a minerology log is saved (e.g., as shown in FIG. 7). Further, in addition to saving the data, the data, regardless of desired output style (table or log), may be displayed on a display device, such as a computer screen or control unit display.

Figure 9:
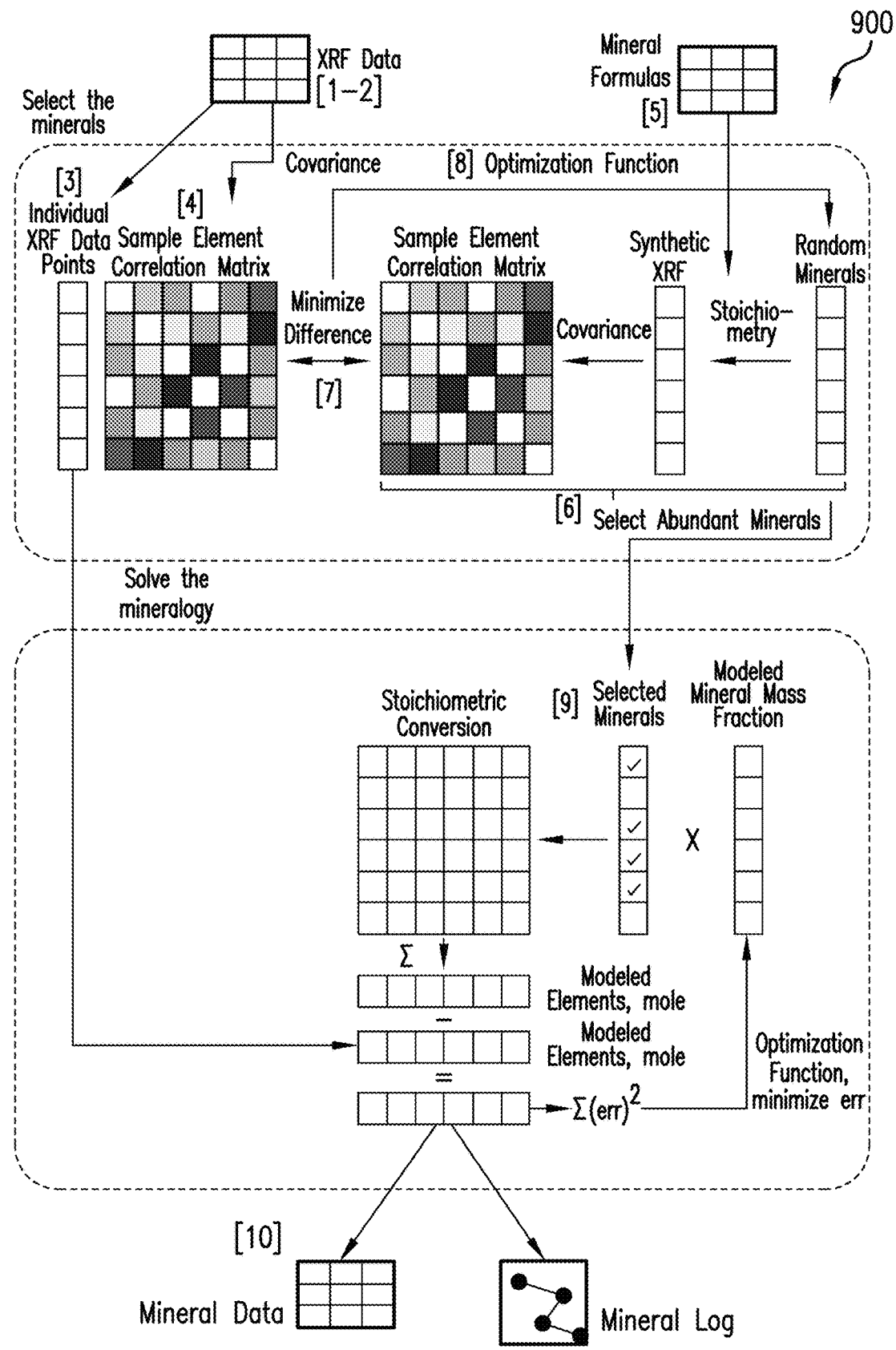
FIG. 9 is a schematic flow chart representing a process for determining a mineral composition of a geologic sample in accordance with an embodiment of the present disclosure.

Turning now to FIG. 9, a schematic flow chart 900 is shown. The flow chart 900 is a graphical form of the flow process 800 of FIG. 8. As shown in FIG. 9, at steps [1-2], XRF data is measured with respect to a geologic sample.

Steps [1-2] include the preparation and measurement processes (e.g., blocks 802, 804 of flow process 800). Step [3] of flow chart 900 represents the conversion of the measured XRF data from the geologic sample into a vector or table of element abundances (e.g., block 806 of flow process 800). At step [4] of the flow chart 900, the XRF data of the geologic sample is converted into a measurement correlation matrix (e.g., blocks 808-810 of flow process 800). In this illustrative depiction, the measurement correlation matrix is represented as a grayscale gradient that is representative of the positive or negative relationship between different elements within the geologic sample. In this illustrative example, white represents a correlation value of +1 and black represents a correlation value of −1. Depending on the specific output and display, different colors (when color coded) or greyscales can be used to indicate either positive or negative correlation.

At step [5], a mineral dictionary is imported into the system (e.g., block 812 of flow process 800). The mineral dictionary may be imported during the measurement process (steps [1-2]), before such measurements, or after the measurements. That is, the obtaining of the mineral dictionary is independent from the measurement and pre-processing steps. At step [6], an artificial correlation matrix is calculated based on a selected initial mineral abundance set (e.g., block 814 of flow process 800). At step [7] of flow chart 900, the measurement correlation matrix and the artificial correlation matrix are compared to output an error value (e.g., block 816 of flow process 800). At step [8] of flow chart 900, the selection of minerals from the mineral dictionary for the artificial correlation matrix is adjusted and the comparison is repeated to minimize the error value (e.g., blocks 818, 814-816 of flow process 800). Once the error value is minimized (e.g., below a predetermined error value or within a predetermined range of error values), the flow chart 900 precedes steps [9]-[10] to solve and output the mineralogy of the geologic sample (e.g., block 820 of flow process 800). Subsequently, the solved mineralogy may be displayed, stored, or otherwise used by an operator or subsequent data-processing system. For example, additional optimization may be performed (e.g., block 828 of flow process 800).

The determined mineral composition of the geologic sample may then be used for downstream processes and/or decision-making. For example, the mineral composition can be used to, for example and without limitation, (i) make geomechanical inferences regarding formation structure, strength, etc., (ii) perform a brittleness analysis to inform fracing operations and deployment, (iii) provide indicators of subsurface formations and reservoirs for production and extraction, and (iv) inform log data interpretation for logs obtained during while-drilling operations.

Although described with respect to x-ray fluorescence, embodiments of the present disclosure are not so limited. Embodiments of the present disclosure are directed to determining a mineral composition of a geologic sample from base element data obtained regarding the sample. Embodiments of the present disclosure may be based on or employ any type of elemental spectroscopy. Example types of element spectroscopy include, without limitation, neutron capture spectroscopy logging, Reitveld refinement (XRD), Raman spectroscopy, infrared spectroscopy, hyperspectral imaging, x-ray spectroscopy (e.g., energy dispersive x-ray spectroscopy), mass spectroscopy, atomic emission spectroscopy, high performance liquid chromatography, gas chromatography, wet chemical analyses (e.g., titration), laser induced breakdown spectroscopy, etc. Furthermore, in accordance with some embodiments, the above described processes may be combined with other types of measurements and data, which can include, without limitation, gamma ray spectroscopy, neutron density, resistivity, nuclear magnetic resonance, etc. That is, various different types of methods and processes may be employed to collected elemental and/or mineral data and various different types of methods and processes of data inversion technologies and methods may be employed without departing from the scope of the present disclosure.

Advantageously, embodiments of the present disclosure enable the determination of downhole mineralogy from a relatively small sample set. The data-driven element-to-mineral model, in accordance with embodiments of the present disclosure does not require prior experience or a subject-matter expertise to determine what constituents should be included in the inversion model. In contrast, embodiments of the present disclosure allow for the use of a library of potential constituents which may or may not be included in the final elemental inversion.

Further, advantageously, embodiments of the present disclosure only need elemental datasets. That is, there is no requirement for supplementary data (e.g., gamma spectroscopy) to determine mineral constituents of a geologic sample. Furthermore, by using artificial correlation matrices with statistically determined populations, natural processes and analytical variability may be achieved. Finally, because of the iterative process and comparison based on correlation matrices, embodiments of the present disclosure do not require large datasets to build the model, as compared to prior or alternative machine-based processes.

In one example of the above described processes, the data-driven element-to-mineral model was tested with laboratory X-ray Fluorescence (XRF) datasets on several geologic reference materials. Datasets fed into the model consisted of at least one hundred XRF measurements. The data-driven element-to-mineral model, in accordance with embodiments of the present disclosure, was able to determine if alumina/silicates belong to feldspars or clays, if there should be any quartz, and the types of carbonates that might be present in the geologic sample. Using correlation to select constituents, combined with the elemental inversion, embodiments of the present disclosure are capable of being employed for end-member mineral determinations and for mixtures.

While embodiments described herein have been described with reference to specific figures, it will be understood that various changes may be made and equivalents may be substituted for elements thereof without departing from the scope of the present disclosure. In addition, many modifications will be appreciated to adapt a particular instrument, situation, or material to the teachings of the present disclosure without departing from the scope thereof. Therefore, it is intended that the disclosure not be limited to the particular embodiments disclosed, but that the present disclosure will include all embodiments falling within the scope of the appended claims or the following description of possible embodiments.

Embodiment 1: A method for determining mineral compositions of material, the method comprising: obtaining elemental data associated with a geologic sample; calculating a measurement correlation matrix of the geologic sample from the elemental data; calculating an artificial correlation matrix; comparing the measurement correlation matrix and the artificial correlation matrix to determine an error value; minimizing the error value by updating the artificial correlation matrix and comparing the measurement correlation matrix to the updated artificial correlation matrix; and determining a mineral composition of the geologic sample based on the minimized measurement correlation matrix.

Embodiment 2: The method according to any preceding embodiment, wherein the geologic sample is obtained from a core sample, the method further comprising: slabbing the core sample with a slabbing saw to expose a surface of the core sample; cleaning the exposed surface; and performing x-ray fluorescence on the cleaned and exposed surface.

Embodiment 3: The method according to any preceding embodiment, wherein the geologic sample is obtained from a sidewall core sample, the method further comprising: trimming the sidewall core sample to expose a surface of the sidewall core sample; cleaning the exposed surface; and performing x-ray fluorescence on the cleaned and exposed surface.

Embodiment 4: The method according to any preceding embodiment, wherein the geologic sample is a cuttings sample, the method further comprising: washing the cuttings sample; drying the cuttings sample; grinding the cuttings sample into powder; pressing the powder into a pellet; performing x-ray fluorescence on a surface of the pellet.

Embodiment 5: The method according to any preceding embodiment, further comprising generating a table of elemental abundances from the x-ray fluorescence data representative of elements that comprise the geologic sample.

Embodiment 6: The method according to any preceding embodiment, further comprising importing a mineral dictionary, wherein the mineral dictionary comprises a plurality of mineral names and associated chemical formulae.

Embodiment 7: The method according to any preceding embodiment, wherein the artificial correlation matrix is based on information in the mineral dictionary.

Embodiment 8: The method according to any preceding embodiment, further comprising incorporating artificially generated signal noise into the artificial correlation matrix.

Embodiment 9: The method according to any preceding embodiment, further comprising repeating minimizing step until the error value is equal to or below a predetermined error value.

Embodiment 10: The method according to any preceding embodiment, wherein the error value is a number between 0 and 1, and wherein the predetermined error value is 0.1.

Embodiment 11: The method according to any preceding embodiment, further comprising ranking a plurality of minerals that comprise the mineral composition of the geologic sample based on mineral abundance.

Embodiment 12: The method according to any preceding embodiment, further comprising saving the mineral composition of the geologic sample in the form of at least one of a mineralogy log and a mineralogy table.

Embodiment 13: The method according to any preceding embodiment, further comprising performing a secondary optimization on the mineral composition of the geologic sample using selected minerals to calculate mineral abundances.

Embodiment 14: The method according to any preceding embodiment, wherein the determining of the mineral composition of the geologic sample is performed during a drilling operation.

Embodiment 15: The method according to any preceding embodiment, wherein the mineral composition of the geologic sample is used to at least one of (i) make geomechanical inferences regarding formation structure, strength, etc., (ii) perform a brittleness analysis to inform fracing operations and deployment, (iii) provide indicators of subsurface formations and reservoirs for production and extraction, and (iv) inform log data interpretation for logs obtained during while-drilling operations.

Embodiment 16: The method according to any preceding embodiment, wherein the elemental data is obtained from X-Ray Fluorescence.

Embodiment 17: The method according to any preceding embodiment, wherein the elemental data is obtained from elemental spectroscopy.

Embodiment 18: The method according to any preceding embodiment, wherein the elemental spectroscopy is Neutron Capture Spectroscopy logging.

Embodiment 19: The method according to any preceding embodiment, wherein the elemental spectroscopy is Reitveld Refinement x-ray diffraction.

Embodiment 20: The method according to any preceding embodiment, further comprising combining the elemental spectroscopy with at least one of gamma ray spectroscopy, neutron density, resistivity, and nuclear magnetic resonance.

In support of the teachings herein, various analysis components may be used including a digital and/or an analog system. For example, controllers, computer processing systems, and/or geo-steering systems as provided herein and/or used with embodiments described herein may include digital and/or analog systems. The systems may have components such as processors, storage media, memory, inputs, outputs, communications links (e.g., wired, wireless, optical, or other), user interfaces, software programs, signal processors (e.g., digital or analog) and other such components (e.g., such as resistors, capacitors, inductors, and others) to provide for operation and analyses of the apparatus and methods disclosed herein in any of several manners well-appreciated in the art. It is considered that these teachings may be, but need not be, implemented in conjunction with a set of computer executable instructions stored on a non-transitory computer readable medium, including memory (e.g., ROMs, RAMs), optical (e.g., CD-ROMs), or magnetic (e.g., disks, hard drives), or any other type that when executed causes a computer to implement the methods and/or processes described herein. These instructions may provide for equipment operation, control, data collection, analysis and other functions deemed relevant by a system designer, owner, user, or other such personnel, in addition to the functions described in this disclosure. Processed data, such as a result of an implemented method, may be transmitted as a signal via a processor output interface to a signal receiving device. The signal receiving device may be a display monitor or printer for presenting the result to a user. Alternatively, or in addition, the signal receiving device may be memory or a storage medium. It will be appreciated that storing the result in memory or the storage medium may transform the memory or storage medium into a new state (i.e., containing the result) from a prior state (i.e., not containing the result). Further, in some embodiments, an alert signal may be transmitted from the processor to a user interface if the result exceeds a threshold value.

Furthermore, various other components may be included and called upon for providing for aspects of the teachings herein. For example, a sensor, transmitter, receiver, transceiver, antenna, controller, optical unit, electrical unit, and/or electromechanical unit may be included in support of the various aspects discussed herein or in support of other functions beyond this disclosure.

The use of the terms "a" and "an" and "the" and similar referents in the context of describing the invention (especially in the context of the following claims) are to be construed to cover both the singular and the plural, unless otherwise indicated herein or clearly contradicted by context. Further, it should be noted that the terms "first," "second," and the like herein do not denote any order, quantity, or importance, but rather are used to distinguish one element from another. The modifier "about" used in connection with a quantity is inclusive of the stated value and has the meaning dictated by the context (e.g., it includes the degree of error associated with measurement of the particular quantity).

It will be recognized that the various components or technologies may provide certain necessary or beneficial functionality or features. Accordingly, these functions and features as may be needed in support of the appended claims and variations thereof, are recognized as being inherently included as a part of the teachings herein and a part of the present disclosure.

The teachings of the present disclosure may be used in a variety of well operations. These operations may involve using one or more treatment agents to treat a formation, the fluids resident in a formation, a borehole, and/or equipment in the borehole, such as production tubing. The treatment agents may be in the form of liquids, gases, solids, semi-solids, and mixtures thereof. Illustrative treatment agents include, but are not limited to, fracturing fluids, acids, steam, water, brine, anti-corrosion agents, cement, permeability modifiers, drilling muds, emulsifiers, demulsifiers, tracers, flow improvers etc. Illustrative well operations include, but are not limited to, hydraulic fracturing, stimulation, tracer injection, cleaning, acidizing, steam injection, water flooding, cementing, etc.

While embodiments described herein have been described with reference to various embodiments, it will be understood that various changes may be made and equivalents may be substituted for elements thereof without departing from the scope of the present disclosure. In addition, many modifications will be appreciated to adapt a particular instrument, situation, or material to the teachings of the present disclosure without departing from the scope thereof. Therefore, it is intended that the disclosure not be limited to the particular embodiments disclosed as the best mode contemplated for carrying the described features, but that the present disclosure will include all embodiments falling within the scope of the appended claims.

Accordingly, embodiments of the present disclosure are not to be seen as limited by the foregoing description, but are only limited by the scope of the appended claims.

What is claimed:

1. A method for determining mineral compositions of a material, the method comprising:
   obtaining elemental data associated with a geologic sample;
   calculating a measurement correlation matrix of the geologic sample from the elemental data;
   calculating an artificial correlation matrix;
   comparing the measurement correlation matrix and the artificial correlation matrix to determine an error value;
   minimizing the error value by updating the artificial correlation matrix to generate an updated artificial correlation matrix and comparing the measurement correlation matrix to the updated artificial correlation matrix; and
   determining a mineral composition of the geologic sample based on the minimized error value.

2. The method of claim 1, further comprising:
   slabbing the geologic sample to expose a surface of the geologic sample;
   cleaning the exposed surface of the geological sample; and
   performing x-ray fluorescence on the cleaned exposed surface of the geological sample.

3. The method of claim 1, further comprising:
   trimming the geologic sample to expose a surface of the geologic sample;
   cleaning the exposed surface of the geological sample; and
   performing x-ray fluorescence on the cleaned exposed surface of the geological sample.

4. The method of claim 1, further comprising:
   grinding the geologic sample into powder;
   pressing the powder into a pellet;
   performing x-ray fluorescence on a surface of the pellet.

5. The method of claim 1, further comprising generating the elemental data from x-ray fluorescence data representative of elements that comprise the geologic sample.

6. The method of claim 1, further comprising importing a mineral dictionary, wherein the mineral dictionary comprises a plurality of mineral names and associated chemical formulae.

7. The method of claim 6, wherein the artificial correlation matrix is based on information in the mineral dictionary.

8. The method of claim 7, further comprising incorporating an artificially generated signal noise into the artificial correlation matrix.

9. The method of claim 1, further comprising repeating the minimizing the error value until the error value is equal to or below a predetermined error value.

10. The method of claim 1, wherein the geologic sample is at least one of a core sample, a sidewall core sample, and a cuttings sample.

11. The method of claim 1, further comprising ranking a plurality of minerals that comprise the mineral composition of the geologic sample based on a mineral abundance.

12. The method of claim 1, further comprising saving the mineral composition of the geologic sample in a form of at least one of a mineralogy log and a mineralogy table.

13. The method of claim 1, further comprising performing a secondary optimization on the mineral composition of the geologic sample using selected minerals to calculate mineral abundances.

14. The method of claim 1, wherein the determining of the mineral composition of the geologic sample is performed during a drilling operation.

15. The method of claim 1, further comprising, based on wherein the mineral composition of the geologic sample, at least one of:
   making geomechanical inferences regarding at least one of a formation structure and a formation strengths;
   performing a brittleness analysis to inform fracing operations and deployment;
   providing indicators of subsurface formations and reservoirs for production and extraction; and
   performing a log data interpretation for logs obtained during while-drilling operations.

16. The method of claim 1, wherein the elemental data is obtained from x-ray fluorescence.

17. The method of claim 1, wherein the elemental data is obtained from elemental spectroscopy.

18. The method of claim 17, wherein the elemental spectroscopy is neutron capture spectroscopy logging.

19. The method of claim 17, wherein the elemental spectroscopy is Reitveld refinement x-ray diffraction.

20. The method of claim 17, further comprising combining the elemental spectroscopy with at least one of gamma ray spectroscopy, a neutron density, a resistivity, and nuclear magnetic resonance.

* * * * *